United States Patent
Walak et al.

(10) Patent No.: US 12,414,678 B2
(45) Date of Patent: Sep. 16, 2025

(54) MEDICAL DEVICE CONTROL MECHANISM AND METHODS OF USE

(71) Applicant: Boston Scientific Scimed, Inc., Maple Grove, MN (US)

(72) Inventors: Steven E. Walak, Natick, MA (US); Bridget Stanford, Reading, MA (US); Priya Vasdev Khanchandani, Shrewsbury, MA (US); Seamus Finbarr O'Shaughnessy, Chelmsford, MA (US); Michael E. Zupkofska, Rockland, MA (US); Heather Bourassa, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 379 days.

(21) Appl. No.: 17/815,618

(22) Filed: Jul. 28, 2022

(65) Prior Publication Data

US 2023/0042812 A1 Feb. 9, 2023

Related U.S. Application Data

(60) Provisional application No. 63/228,866, filed on Aug. 3, 2021.

(51) Int. Cl.
*A61B 1/005* (2006.01)
*A61B 1/00* (2006.01)
(Continued)

(52) U.S. Cl.
CPC ........ *A61B 1/0057* (2013.01); *A61B 1/00135* (2013.01); *A61B 1/0052* (2013.01);
(Continued)

(58) Field of Classification Search
CPC .............. A61B 1/0627; A61B 1/00096; A61B 1/00183; A61B 1/06; A61B 1/05;
(Continued)

(56) References Cited

U.S. PATENT DOCUMENTS

| | | | |
|---|---|---|---|
| 4,926,257 A | 5/1990 | Miyazaki | |
| 7,999,945 B2 | 8/2011 | Zara | |
| 9,693,707 B2 | 7/2017 | Chan et al. | |
| 10,646,107 B2 | 5/2020 | Matthison-Hansen et al. | |
| 10,849,483 B2 | 12/2020 | Farr et al. | |
| 10,905,320 B2 | 2/2021 | Levy | |
| 2007/0223898 A1 | 9/2007 | Purwanto | |

(Continued)

FOREIGN PATENT DOCUMENTS

| | | |
|---|---|---|
| CN | 106132274 B | 8/2018 |
| DE | 102013211698 | 7/2017 |

(Continued)

OTHER PUBLICATIONS

International Search Report and Written Opinion issued in International Application No. PCT/US2022/074230, issued Nov. 21, 2022 (24 pages).

*Primary Examiner* — Michael J Carey
*Assistant Examiner* — Timothy Tuan Luu
(74) *Attorney, Agent, or Firm* — Bookoff McAndrews, PLLC (57) ABSTRACT

A medical device including a handle including an actuation device, a sheath extending from the handle and having a longitudinal axis, the sheath defining an imaging lumen extending from the handle to a distal end of the sheath, an imaging device at a distal end of the sheath, and a piezoelectric member connected to the imaging device, where movement of the piezoelectric member moves the imaging device in a first direction relative to the longitudinal axis.

15 Claims, 5 Drawing Sheets

(51) Int. Cl.
*A61B 1/008* (2006.01)
*A61B 1/015* (2006.01)
*A61B 1/018* (2006.01)
*A61B 1/05* (2006.01)
*A61B 1/06* (2006.01)

(52) U.S. Cl.
CPC ............ *A61B 1/0055* (2013.01); *A61B 1/008* (2013.01); *A61B 1/015* (2013.01); *A61B 1/018* (2013.01); *A61B 1/05* (2013.01); *A61B 1/06* (2013.01)

(58) Field of Classification Search
CPC ......... A61B 1/018; A61B 1/015; A61B 1/008; A61B 1/0055; A61B 1/0052; A61B 1/00135; A61B 1/0057; A61B 1/0004; A61B 1/0058
USPC ................ 600/103, 109, 160, 171, 173, 174
See application file for complete search history.

(56) References Cited

U.S. PATENT DOCUMENTS

| | | | |
|---|---|---|---|
| 2010/0121143 A1* | 5/2010 | Sugimoto | A61B 1/00167 600/109 |
| 2014/0024931 A1 | 1/2014 | Winston et al. | |
| 2019/0117044 A1* | 4/2019 | Anderson | A61B 1/051 |
| 2019/0216325 A1 | 7/2019 | OuYang | |
| 2019/0246873 A1 | 8/2019 | Lu et al. | |
| 2019/0328217 A1* | 10/2019 | Moreau | A61B 1/00183 |
| 2020/0046209 A1* | 2/2020 | Fancher | A61B 1/05 |
| 2020/0221936 A1 | 7/2020 | Raj et al. | |

FOREIGN PATENT DOCUMENTS

| | | | |
|---|---|---|---|
| JP | S6053920 | 3/1985 | |
| JP | 5727373 B2 * | 6/2015 | ........... A61B 1/0019 |
| JP | 6526177 | 6/2019 | |
| JP | 6708705 B2 | 6/2020 | |
| WO | 2016044320 A1 | 3/2016 | |

\* cited by examiner

MEDICAL DEVICE CONTROL MECHANISM AND METHODS OF USE

CROSS-REFERENCE TO RELATED APPLICATIONS

This application claims the benefit of priority of U.S. Provisional Patent Application No. 63/228,866, filed Aug. 3, 2021, the entirety of which is incorporated herein by reference.

TECHNICAL FIELD

This disclosure relates generally to medical devices and related methods of use. More particularly, in some embodiments, the disclosure relates to changing a field of view of an imaging device of an endoscopic medical device.

BACKGROUND

Medical tools for accessing target sites within a body may be advanced through one or more lumens of an endoscope, and may extend from a distal end thereof to manipulate the target site. Drawbacks of these endoscopic systems include, for example, limited ability for a single scope to provide both a side-view and an end-view of the target site. For example, in many endoscopes (or medical tools inserted through an endoscope), the imaging device is either side-facing or front-facing and therefore provides either a view towards a side of the endoscope or a view forward of the endoscope. This limits the ability to view the target site from multiple orientations of the distal end of the endoscope. This may create difficulties in medical procedures by limiting the field of view of the target site. Furthermore, it may be necessary to use multiple devices, such as multiple imaging devices, to provide the necessary number of fields of view of the target site, which may increase the size of the endoscope system and/or the duration of the procedure. This may increase the risk of accidents, infections, or other complications. This disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes a handle having an actuation device, a sheath extending from the handle and having a longitudinal axis, the sheath defining an imaging lumen extending from the handle to a distal end of the sheath, an imaging device at a distal end of the sheath, and a piezoelectric member connected to the imaging device, wherein movement of the piezoelectric member moves the imaging device in a first direction relative to the longitudinal axis.

A plate may be positioned within the imaging lumen and may fluidly seal a proximal end of the imaging lumen from a distal end of the imaging lumen, and wherein the piezoelectric member may be connected to a distal facing surface of the plate.

A flexible member may fluidly seal an opening at the distal end of the imaging lumen, wherein a distal end of the piezoelectric members may be connected at a proximal facing surface of the flexible member, wherein the imaging device may be connected to a distal facing surface of the flexible member, and wherein movement of the piezoelectric member may cause the flexible member to bend relative to the longitudinal axis.

The piezoelectric member may expand from a first position, where a distal end of each of the piezoelectric member may be disposed proximal to an opening in a distalmost end of the imaging lumen, to a second position, where the distal end of each of the piezoelectric member may be positioned distal to the opening.

The distal end of the piezoelectric member may be connected to the imaging device, and wherein movement from the first position to the second position may move the imaging device from a position proximal to the distal end of the sheath to a position distal of the distalmost end of the sheath.

The medical device may further include a second piezoelectric member, wherein movement of the second piezoelectric member may move the imaging device in a second direction relative to the longitudinal axis, different from the first direction, and wherein the sheath may further comprise a working channel extending from the handle and terminating at an opening at a distalmost end of the sheath.

A viewing area of the imaging device may include a portion of the opening of the working channel when the imaging device is moved in one of the first direction or the second direction.

The imaging device may include at least one of an imager and a light emitting element.

The medical device may further include a flexible member fluidly sealing an opening at the distal end of the imaging lumen, wherein the distal end of each of the piezoelectric members may be connected at a proximal facing surface of the flexible member, wherein the imaging device may be connected to a distal facing surface of the flexible member, wherein movement of the piezoelectric members may cause the flexible member to bend relative to the longitudinal axis such that the imaging device may image the opening in the working channel and a radially outer surface of the distal end face of the sheath.

The piezoelectric members may be configured to bend the flexible member in the first direction and the second direction at a same time.

The medical device may further include a plurality of imaging devices, wherein a first imaging device from the plurality of imaging devices may image the opening at a same time a second imaging device from the plurality of imaging devices images the radially outer surface of the distal end face.

A distal portion of the sheath may include an articulation joint including a plurality of links, and wherein the piezoelectric member may include a first set of piezoelectric members attached to and between adjacent links on a first side of the articulation joint, and a second set of piezoelectric members attached to and between the adjacent links on a second side of the articulation joint, wherein the first side and the second side may be offset 180 degrees about the sheath.

The medical device may further include a working channel extending from the handle and terminating at an opening at a distal end face of the articulation joint, the working channel may be configured to receive one or more of a medical instrument, a fluid, or a suction.

Each piezoelectric member from the plurality of piezoelectric members may be individually controlled such that an angle of articulation joint relative to the longitudinal axis may be changed.

The piezoelectric member may be in a rest state when a voltage is not supplied to the piezoelectric member, and each of the piezoelectric members may change at least one of a shape, a size, or a direction when the voltage is supplied to the piezoelectric member.

According to another aspect, a medical device includes a handle including an actuation device, wherein the actuation device controls supply of a voltage, a sheath extending from the handle and having a longitudinal axis, an articulation joint connected to a distal end of the sheath, the articulation joint having a plurality of connected links, an imaging device at a distal end of the articulation joint, a first set of piezoelectric members attached to and between adjacent links on a first side of the articulation joint, and a second set of piezoelectric members attached to and between the adjacent links on a second side of the articulation joint.

The piezoelectric members from each of the first set of piezoelectric members and the second set of piezoelectric members may be independently controlled such that (1) the articulation joint bends at different angles between adjacent sets of links, and (2) the articulation joint bends in different directions relative to the longitudinal axis between adjacent sets of links.

The handle may further include a second actuation device, wherein actuation of the first actuation device may supply a voltage to the piezoelectric members of the first set of piezoelectric members, and wherein actuation of the second actuation device may supply a voltage to the piezoelectric members of the second set of piezoelectric members.

According to another aspect, a method includes inserting a shaft of an insertion device into a body via an opening, advancing the insertion device so that a distal end of the insertion device is adjacent to a target site, supplying a voltage to at least one piezoelectric member to change a viewing angle of an imaging device attached to the insertion device, wherein the viewing angle is changed toward or away from a central longitudinal axis of the insertion member, and advancing a medical instrument through a lumen of the insertion device and out of an opening in a distal end of the insertion device to perform a medical procedure.

The method may further include supplying a first voltage to a first piezoelectric member from the at least one piezoelectric member to cause a first portion of the insertion device to be angled at a first angle relative to the central longitudinal axis, and supplying a second voltage, different from the first voltage, to a second piezoelectric member from the at least one piezoelectric member to cause a second portion of the insertion device, different from the first portion, to be angled at a second angle relative to the central longitudinal axis, wherein the second angle is different from the first angle.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

This disclosure is described with reference to exemplary medical systems and medical tools for viewing a target site, for example, for viewing a target site by varying an imaging device's position, direction, and/or field of view, relative to the target site and other portions of a distal end of an endoscope. This may provide improved medical tool functionality and/or assist medical professionals to gain improved viewing of, and access to, the target site for performing medical procedures. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer to exact and approximate shapes.

Figure 1:
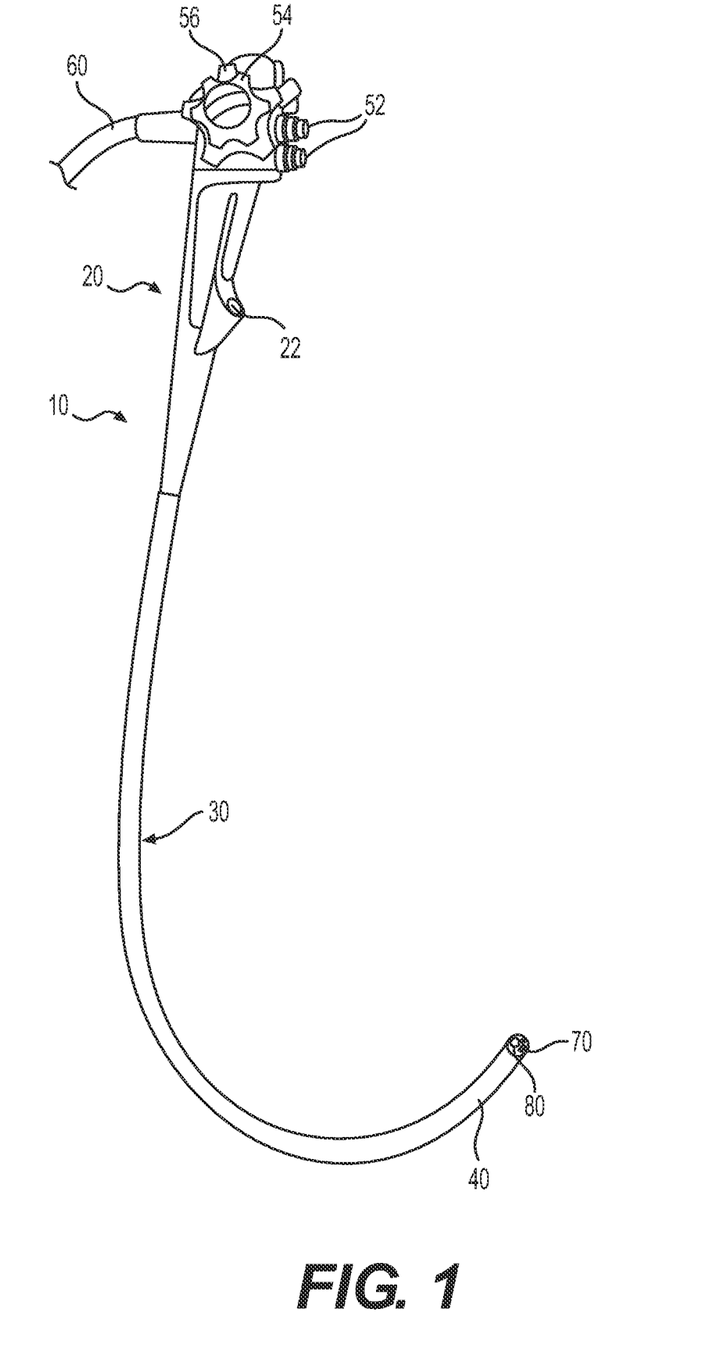
FIG. 1 is a schematic view of an endoscope system according to an embodiment.

Referring to FIG. 1, a medical system 10 according to an embodiment is shown. Medical system 10 may include a handle 20, a shaft 30 (e.g., a catheter) connected to a distal end of handle 20, a distal end 40 at a distal end of shaft 30, and an umbilicus 60 extending from a proximal end of handle 20. Distal end 40 may include one or more of an articulation joint, an end effector, an imaging device, light elements, openings for suction/irrigation/insufflation/accessory devices, etc. Shaft 30 may be flexible and may be formed of any medical grade material suitable for accessing a tortuous path within the body, but the rigidity/flexibility of shaft 30 is not limited. Medical system 10 may be an endoscope, a colonoscope, a bronchoscope, an ureteroscope, a duodenoscope, or other like-device.

With continued reference to FIG. 1, handle 20 may include first and second actuating devices 54, 56. Devices 54, 56 may control one or more elements that extend through shaft 30 and connect to distal end 40. Actuating devices 54, 56 may be, for example, rotatable knobs that rotate about their axes to push/pull actuating elements (e.g., wires, not shown) which extend within one or more lumens of shaft 30. Rotation of actuating devices 54, 56 may cause shaft 30 and/or distal end 40 to bend relative to longitudinal axis A (FIG. 2), via an articulating joint. Alternatively or additionally, actuating elements may, e.g., close or open a forceps, rotate an end effector about a longitudinal axis A, raise or lower an elevator, or provide other functionality to an end effector. Handle 20 may also include actuating devices 52. Though two actuating devices are shown, more than two devices 52 may be used for the various functionalities desired. For example, in embodiments, one or more of actuating devices 52 may control the supply of air and/or water to distal end 40. Additionally, one or more of actuating devices may control a device 70 at distal end 40 to control a position or orientation of light emitting and/or imaging devices 100. For example, actuating devices 52 may be push buttons or the like which may control activation of light emitting or imaging devices 100. Actuating devices 52 may also control supply of voltage to a piezoelectric member (e.g., piezoelectric members 120a, 120b in FIG. 2) to control movement of control device and therefore a position or a direction of elements on control device 70, as described herein. For example, depressing one of actuating devices 52 may cause a supply of voltage to piezoelectric member 120a, 120b and cause control device 70 to move in a first direction, while pressing another of actuating devices 52 may end the supply of voltage and/or supply a different amount of voltage to the same or another piezoelectric member 120a, 120b, to cause control device 70 to move in an opposite or different direction. Umbilicus 60 may include light and/or control cables or wires to control light emitting and/or imaging devices 100. Umbilicus 60 may extend from handle 20 and may be connected to a display, a controller, or other similar device.

Figure 2:
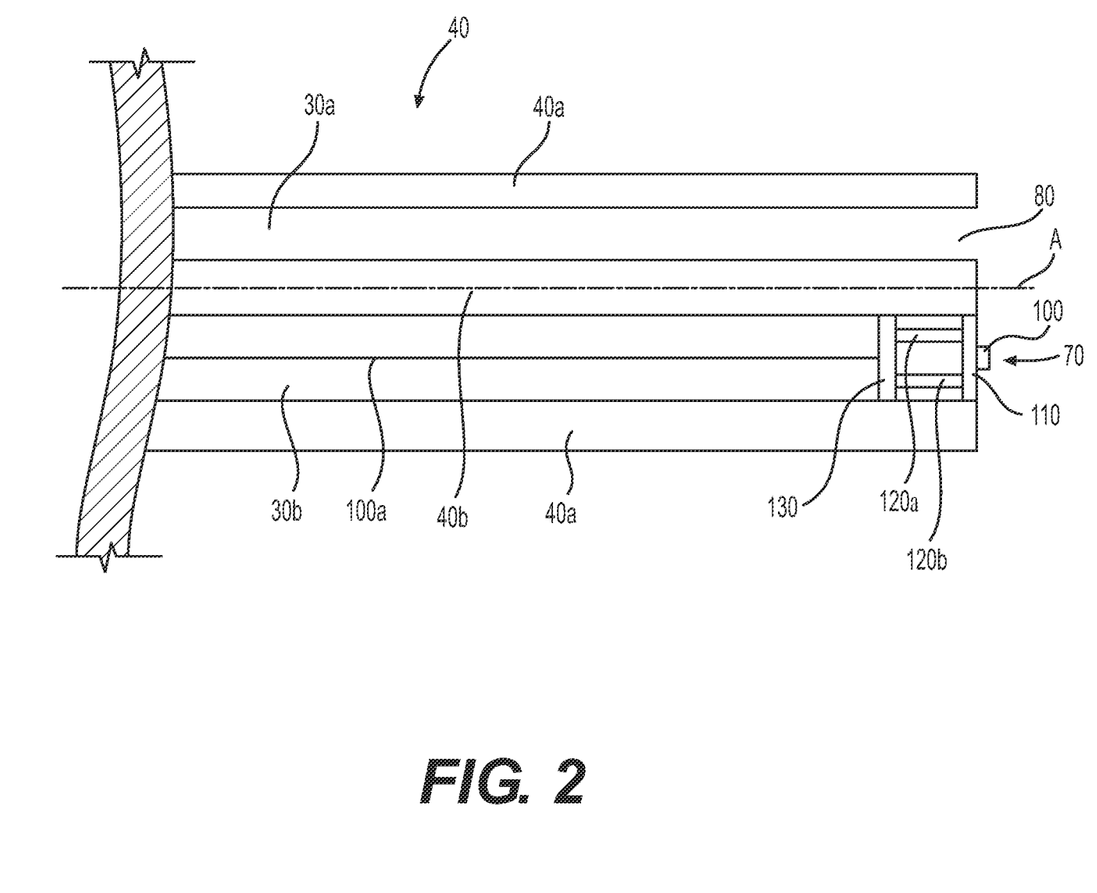
FIG. 2 is a cross-sectional view of a distal end of the endoscope system of FIG. 1, according to an embodiment.

Handle 20 may also include an opening 22 which may be fluidly connected to one or more lumens of shaft 30 (e.g., a working channel 30a shown in FIG. 2). For example, a medical instrument (not shown) may be inserted into opening 22 and may be extended to distal end 40. An opening 80 at a distalmost end of distal end 40 may be fluidly coupled to opening 22, and the medical instrument may be extended from opening 80. Alternatively, or additionally, fluid may be supplied to a target site via opening 80, or suction may be supplied via opening 22 to remove debris from the target site via opening 80.

With reference to FIG. 2, distal end 40 includes an outer wall 40a (e.g., annular shaped) and an inner wall 40b within outer wall 40a. A working channel 30a (e.g., a first lumen) is defined between outer wall 40a and a first surface of inner wall 40b. Working channel 30a may terminate in opening 80 at the distalmost end of distal end 40. As described herein, medical instruments, fluid, or suction may be supplied to a target site via working channel 30a.

An imaging channel 30b (e.g., a second lumen) is defined between outer wall 40a and a second surface of inner wall 40b. One or more cables 100a may extend from handle 20 through imaging channel 30b and may be connected at a distal end to a proximal member 130 which may include a controller, circuitry, or other control elements for controlling a position of control device 70 and, thus, a position of light emitting and/or imaging devices 100 connected directly or indirectly to control device 70. It will be understood that outer wall 40a and inner wall 40b may be a unitary member having working channel 30a and imaging channel 30b formed therethrough. It will also be understood that imaging channel 30b is not limited to imaging cables, and may include cables for controlling light emitting and imaging devices 100 and/or a movement of control device 70 for controlling a direction of light emitting and imaging devices 100. Proximal member 130 may be connected to outer wall 40a and inner wall 40b and may create a fluid seal between a proximal end and a distal end of imaging channel 30b. In some instances, proximal member 130 may have a same cross-sectional shape as a cross-section of imaging channel 30b and/or may have a same diameter as a cross-sectional diameter of imaging channel 30b. Alternative, or additionally, openings may be formed in proximal member 130 and/or between proximal member 130 and one or both of outer wall 40a and inner wall 40b. This may allow cables (e.g., control cables) to pass to a distal end of shaft 30.

With continued reference to FIG. 2, control mechanism 70 may be disposed at a distal end of imaging lumen 30b. Control mechanism 70 may include proximal member 130 which may be generally perpendicular to a longitudinal axis of imaging lumen 30b. Proximal member 130 may fluidly seal a proximal end of imaging lumen 30b from a distal end thereof. As described herein, proximal member 130 may include a controller, circuitry, or similar mechanism attached thereto.

Control mechanism 70 further includes piezoelectric members 120a, 120b, which may extend distally from proximal member 130. Piezoelectric members 120a, 120b may be cylindrical or may be any other shape. While two piezoelectric members 120a, 120b are shown, any number may be provided, e.g., one, three, four, or more. A distal end of each piezoelectric member 120a, 120b may be connected to a distal plate 110 of control mechanism 70. Distal plate 110 may be entirely disposed within imaging lumen 30b, partially disposed within imaging lumen 30b, or may be entirely disposed distal of a distalmost end of distal end 40. As will be described, piezoelectric members 120a, 120b may move distal plate 110, including moving distal plate 110 proximally into imaging lumen 30b and/or distally relative to the distalmost end of distal end 40.

One or more imaging devices 100 may be attached to a distal facing side of distal plate 110. It will be understood that imaging device 100 may be integrally formed with distal plate 110, or imaging device 100 may replace distal plate 110, e.g., such that piezoelectric members 120a, 120b connect directly to imaging device 100. Imaging device 100 may be one or more light emitting devices (e.g. LEDs), one or more imaging devices (e.g., cameras, including CMOS or CCD imagers), or a combination thereof. While only one imaging device 100 is shown, there may be more than one imaging device 100, e.g., multiple imaging devices, multiple light emitting devices, and/or one or more of each of imaging devices and light emitting devices.

Piezoelectric members 120a, 120b may receive a voltage or a current via cable 100a. For example, a voltage may be supplied to first piezoelectric member 120a, which may cause first piezoelectric member 120a to expand in the distal direction and/or tilt distal plate 110 downwards in FIG. 2 (e.g., at an angle other than perpendicular to longitudinal axis A). Terminating the supply of voltage to first piezoelectric member 120a may cause first piezoelectric member 120a to contract to a rest, or unexpanded, state. For example, a resting state of each piezoelectric member 120a, 120 may be a state in which respective piezoelectric members 120a, 120b are distal facing and not expanded. This may cause device 100 to have a rest state, in which device 100 is distal facing and approximately perpendicular to longitudinal axis A. In some instances, device 100 may image an outer surface of shaft 30 or distal opening 80. Supplying a voltage to second piezoelectric member 120b may similarly cause second piezoelectric member 120b to expand distally, and may cause distal plate 110 to be tilted upward (e.g., at an angle other than perpendicular to longitudinal axis A). Supplying a voltage to both first and second piezoelectric members 120a, 120b may cause distal plate 110 to move in a distal direction, e.g., distal of the distalmost end of distal end 40. Additional piezoelectric members 120 may enable movement in additional directions, e.g., left and right, relative to longitudinal axis A. In this manner, an operator may change a field of view of device 100 to image and/or illuminate different areas of the target site.

Piezoelectric members 120 may include one or more materials, including, for example, zirconate titanate (PZT), barium titanate, and/or lithium niobate. Piezoelectric members 120 may also include a quartz or other naturally-occurring piezoelectric material. Additionally, or alternatively, a polyvinylidene fluoride (PVDF) film may be applied to piezoelectric members 120. The PVDF film may include two layers, each layer having an opposite polarity, which may cause each piezoelectric member 120 to bend. While described as a single member, each piezoelectric member 120 may include two or more piezoelectric stacks, e.g., multiple piezoelectric members stacked together, micromotors, and/or amplified actuators, which may cause greater movement of each piezoelectric member 120 and which may increase a displacement of imaging device 100.

A method of operating medical system 10 will be described. Medical system 10 may be inserted into a body opening (e.g., an incision, a natural orifice, etc.) by inserting distal end 40 through the body opening. Distal end 40 may be advanced to a target site within the body. As distal end 40 is advanced through the body and/or once distal end 40 reaches the target site, a position, an orientation, and/or an angle of one or more devices 100, relative to the target area and/or other components at the distal end 40 of system 10, may be changed. For example, the user of medical system 10 may actuate one or more of actuating devices 52. Actuating device 52 may cause a voltage to be supplied from a power source (not shown) (e.g., a voltage generator, a power outlet, etc.) to one or more piezoelectric members 120a, 120b. Supplying voltage to piezoelectric members 120a, 120b may cause piezoelectric members 120a, 120b to expand and/or contract, which may cause distal plate 110 and, thus, device 100 to change its angle relative to longitudinal axis A (e.g. from perpendicular to axis A to not perpendicular to axis A, including parallel to axis A).

During the medical procedure, voltage may be supplied to one or more of piezoelectric members 120a, 120b to change the angle of device 100 relative to longitudinal axis A based on a desired light and/or viewing angle (including forward facing, side facing, and angles therebetween). In some instances, one or more medical instruments may be advanced to the target site via working channel 30a. Once the medical procedure is complete, medical system 10 may be removed from the body.

Figure 3:
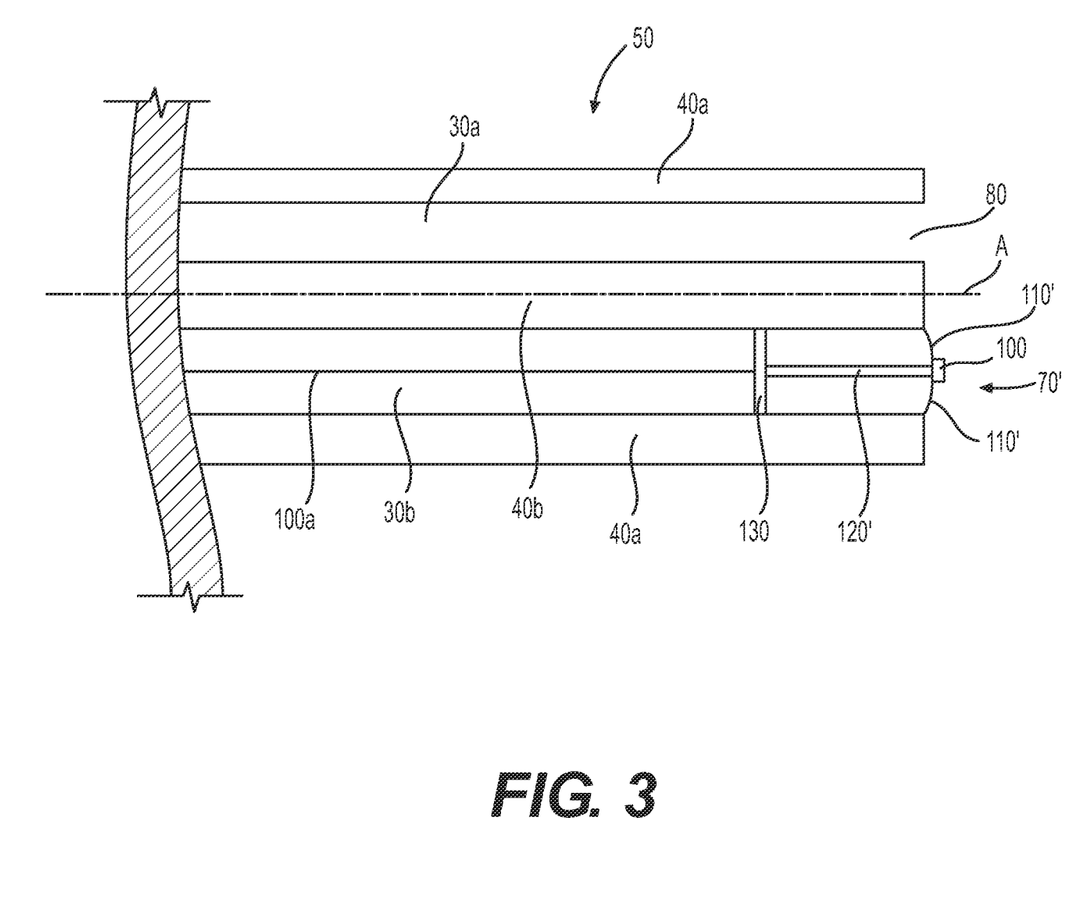
FIG. 3 is a cross-sectional view of a distal end of the endoscope system of FIG. 1, according to another embodiment.

Distal end 40 having another example of a control mechanism 70' is shown in FIG. 3. Similar to distal end 40 in FIG. 2, working channel 30a and imaging lumen 30b may be defined within distal end 40 by inner wall 40b and outer wall 40a. Cable 100a may extend distally from handle 20 and may connect to proximal member 130. As with distal end 40 in FIG. 2, proximal member 130 may be fixed to walls 40a, 40b and fluidly seal the proximal end of imaging lumen 30b from the distal end. A single piezoelectric member 120' may extend distally from, and be fixed to, a distal surface of proximal member 130. Imaging device 100 (which may include one or more imaging devices and/or light emitting devices) may be connected to a distal end of piezoelectric member 120'. As with imaging device 100 in FIG. 2, imaging device 100 may be disposed entirely within imaging lumen 30b, partially within imaging lumen 30b, or distal to a distalmost end of distal end 40. Supplying a voltage to piezoelectric member 120' may cause piezoelectric member 120' to be deflected (e.g., bend) relative to longitudinal axis A, altering the position, orientation, and/or angle of imaging device 100 relative to the treatment area and/or other components at the distal end 40. In this manner, the light and/or imaging field may be changed, which may provide increased fields of view during a medical procedure. It will also be understood that piezoelectric member 120' does not require proximal member 130. For example, piezoelectric member 120' may be connected directly to a wall of imaging lumen 30b. Piezoelectric member 120' may include any material described herein, e.g., zirconate titanate (PZT), barium titanate, lithium niobate, a quartz or other naturally-occurring piezoelectric material. Additionally, or alternatively, a PVDF film may be applied to piezoelectric member 120', as described above. Additionally, or alternatively, piezoelectric member 120' may include two or more piezoelectric stacks, micromotors, and/or amplified actuators, which may cause greater movement of each piezoelectric member 120' as described herein.

A bellows 110' (e.g., a flexible member, including a flexible membrane) may be connected to a perimeter of a distal opening of imaging lumen 30b. Bellows 110' may include a fluid-resistant/impermeable material and may create a fluid seal between imaging lumen 30b and a target site. The flexible material of bellows 110' may allow piezoelectric member 120' to move relative to longitudinal axis A (e.g. bend), while maintaining a fluid seal at the distal end of imaging lumen 30b. In some instances, a voltage may be supplied to piezoelectric member 120', which may cause lateral motion (e.g., side-to-side) of piezoelectric member 120'. An increased supply of voltage may cause a greater bend in piezoelectric member 120'. To move bellows 110' in an up-down direction, a second piezoelectric member 120' (not shown) may be provided and may be rotated 90 degrees relative to piezoelectric member 120'. Supplying voltage to the second piezoelectric member 120' may cause the second piezoelectric member 120' to be deflected laterally in a direction perpendicular to the deflection direction of the first piezoelectric member 120'.

A method of operating medical system 10 will be described. Medical system 10 may be inserted into a body opening (e.g., an incision, a natural orifice, etc.) and advanced to the target site as described with reference to FIG. 2. Distal end 40 may be advanced to a target site within the body. As distal end 40 is advanced through the body and/or once distal end 40 reaches the target site, a position, an orientation, and/or an angle of one or more devices 100, relative to the target area and/or other components at the distal end 40 of system 10, may be changed by actuating devices 52. Supplying voltage to piezoelectric member 120' may cause piezoelectric member 120' to bend from side to side, which may cause bellows 110' to stretch or bend and device 100 to change its angle relative to longitudinal axis A (e.g. from perpendicular to axis A to not perpendicular to axis A, including parallel to axis A). For example, piezoelectric member 120' may have a rest state in which piezoelectric member 120' is parallel to longitudinal axis A and not expanded. This may cause bellows 110' to lie along a plane generally perpendicular to longitudinal axis A. A non-rest position may be a position other than the rest position, e.g., moving piezoelectric member 120' such that piezoelectric member 120' is not parallel to longitudinal axis A and at least a portion of bellows 110' is not perpendicular to longitudinal axis A. Once the medical procedure is complete, medical system 10 may be removed from the body.

Figure 4:
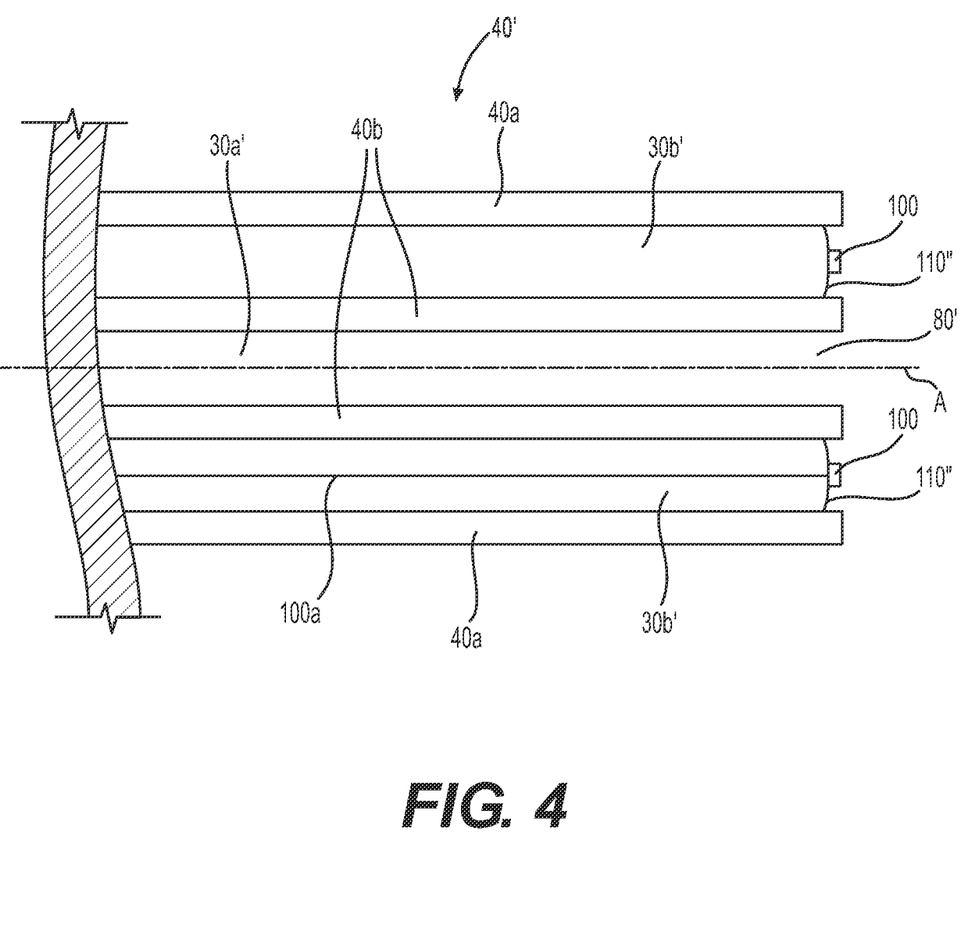
FIG. 4 a cross-sectional view of a distal end of the endoscope system of FIG. 1, according to another embodiment.

Another example of a distal end 40' is shown in FIG. 4, where an annular imaging lumen 30b' may be coaxial with a working channel 30*a*'. For example, outer wall 40*a* and inner wall 40*b* may define imaging lumen 30*b*' having a generally annular cross-section. Inner wall 40*b* may be supported within imaging lumen 30*b*' via protrusions or other connections between walls 40*a*, 40*b* (not shown). Inner wall 40*b* may define working channel 30*a*' having a generally circular cross-section. A distal opening 80' in working channel 30*a*' may allow medical instruments, fluid, suction, or the like to be supplied to or removed from a target site.

A piezoelectric member 110" may fluidly seal a distal end of imaging lumen 30*b*' from the target site. It will be understood that piezoelectric member 110" may include any material described herein, e.g., any material described relative to piezoelectric member 120 and/or piezoelectric member 120'. Piezoelectric material 110" may have an annular shape to fit within lumen 30*b*'. Piezoelectric material 110" can be one integral structure or multiple discrete structures. One or more imaging devices 100 (which may include one or more imaging devices and/or light emitting elements) may be attached to a distal surface of piezoelectric member 110", each device 100 having a resting state facing distally. One or more cables 100*a* may extend from handle 20 and may be connected to a proximal surface of piezoelectric member 110". In embodiments, multiple cables 100*a* can connect to the same piezoelectric material 110". As with the devices shown in FIGS. 2 and 3, supplying a voltage to piezoelectric member 110" may cause piezoelectric member 110" to expand, contract, and/or otherwise change shape. Supplying voltage to piezoelectric member 110" in different locations may also cause one portion of piezoelectric member 110" to tilt radially outward, while supplying voltage to piezoelectric member 110" in a different location may cause piezoelectric member 110" to tilt radially inward. In this manner, an operator may change a field of view of each imaging device 100 and/or illuminate different areas of the target site. It will be understood that piezoelectric member 110" may extend around an entire circumference of the distal opening of imaging lumen 30*b*' (e.g., 360 degrees), or may only extend part way around the circumference of the distal opening of imaging lumen 30*b*' (e.g., 180 degrees, 270 degrees, etc.). While imaging device 100 is shown as being centered on piezoelectric member 110" and distally facing in a rest configuration, i.e., when no voltage is supplied to piezoelectric member 110", it will be understood that the position of imaging device 100 is not limited thereto. For example, imaging device may be positioned radially inward or radially outward from a center of piezoelectric member 110". Additionally, or alternatively, a distal end face of imaging device 100 may be tilted radially inward toward longitudinal axis A, or radially outward away from longitudinal axis A in the rest configuration.

A method of operating medical system 10 will be described. Medical system 10 may be inserted into a body opening (e.g., an incision, a natural orifice, etc.) and advanced to a target site within the body. As distal end 40' is advanced through the body and/or once distal end 40' reaches the target site, a position, an orientation, and/or an angle of one or more devices 100, relative to the target area and/or other components at the distal end 40' of system 10, may be changed by actuating one or more of actuating devices 52 as described with reference to FIG. 2. Supplying a voltage to piezoelectric member 110" may cause piezoelectric member 110" to bend relative to longitudinal axis A. In some instances, a first portion of piezoelectric member 110" may be angled toward longitudinal axis A, while a second, different portion of piezoelectric member 110" may change its angle relative to longitudinal axis A, e.g., toward a radially outer surface of distal end 40 (e.g. from perpendicular to axis A to not perpendicular to axis A, including parallel to axis A). Medical instruments may be advanced to the target site in any manner described herein.

Figure 5A:
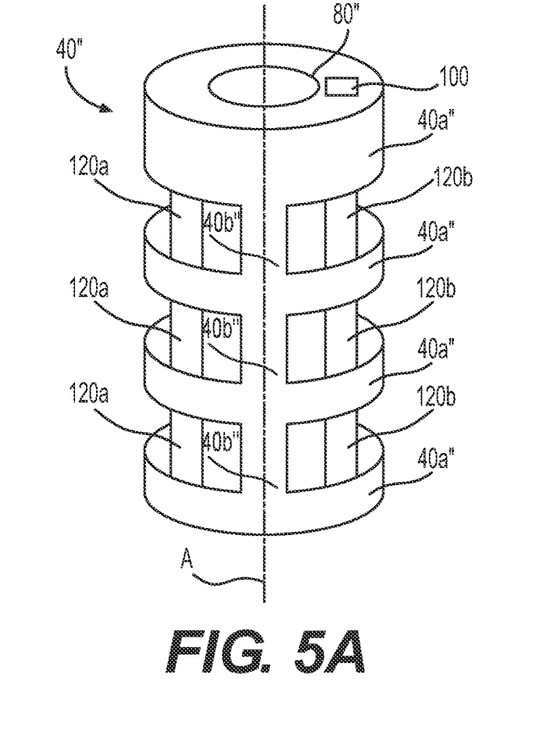
FIGS. 5A and 5B are perspective views of a distal end of the endoscope system of FIG. 1, according to another embodiment.
Figure 5B:
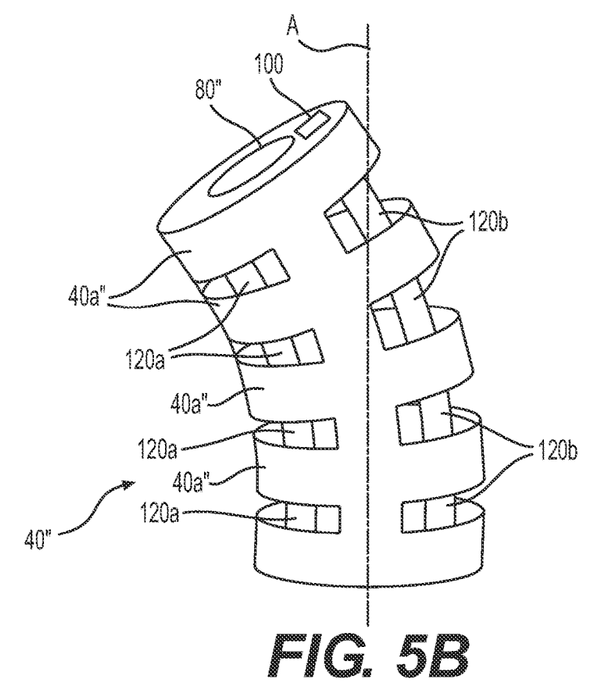

A distal end 40" according to another example is shown in FIGS. 5A and 5B. Distal end 40" may include an articulation joint having a plurality of links 40*a*" joined together at bending locations 40*b*". Distal end 40" may be formed as a unitary member by, e.g., extrusion molding. Alternatively, each link 40*a*" may be joined by a connector, e.g., a spring, at bending locations 40*b*". Distal end 40" may be capable of bending in only two directions along a single plane, as shown in FIG. 5B, based on the orientation of bending location 40*b*". Alternatively, bending locations 40*b*" may be offset 90 degrees about a circumference of distal end 40" for each adjacent set of links 40*a*", which may allow distal end 40" to bend in more than two directions, e.g., four directions along two planes perpendicular to each other. Alternatively, bending locations 40*b*" may include a superelastic material, e.g., Nitinol, which may allow for non-permanent bending of the articulation joint.

It will be understood that distal end 40" may be the distalmost end of a scope (e.g., an endoscope, an ureteroscope, a duodenoscope, etc.). Alternatively, distal end 40" may be proximal to the distalmost end of a medical instrument (such as a scope) or a medical instrument inserted through a working channel of a scope. One or more imaging devices 100 (including one or more imaging device and/or light emitting devices) may be supported on a distal end face of distal end 40". Alternatively, or additionally, an end effector (e.g., forceps, a knife, a snare, etc.) may be attached to the distal end face 40".

Piezoelectric members 120*a*, 120*b* may provide improved control over articulation of the articulation joint at distal end 40". Provided between adjacent links 40*a*" are piezoelectric members 120*a* and 120*b*. Piezoelectric members 120*a* and 120*b* may extend between adjacent links 40*a*" at a radially outermost surface of links 40*a*". Alternatively, piezoelectric members 120*a* and 120*b* may be positioned radially inward from the radially outermost surface. In some instances, piezoelectric members 120*a* and 120*b* may be connected directly to adjacent links, e.g., such that there are multiple, discrete piezoelectric members 120*a* and multiple piezoelectric members 120*b* each independently controlled. For example, one or more control cables may extend from handle 20 to each of piezoelectric members 120*a* and 120*b* and may control expansion and contraction of piezoelectric members 120*a* and 120*b*. Alternatively, each of piezoelectric members 120*a* and 120*b* may each include a rod extending from a proximal end of the articulation joint to the distal end. For example, piezoelectric member 120*a* may be a rod extending from a proximalmost link to a distalmost link on a first side of the articulation joint, and piezoelectric member 120*b* may be a rod extending from the proximalmost link to the distalmost link on a second side of the articulation joint, opposite the first side. It will be understood that piezoelectric members 120*a* and 120*b* may extend along only a portion of the articulation joint, e.g., from a position distal of the proximalmost link or a position proximal of the distalmost link. It will be understood that piezoelectric members 120*a*, 120*b* may include any material described herein, e.g., any material described relative to piezoelectric member 120, piezoelectric member 120', and/or piezoelectric member 110".

As described herein, supplying a voltage to a first set of piezoelectric members 120*a* may cause the first set of piezoelectric members 120a to contract, while supplying a voltage to a second set of piezoelectric members 120b may cause the second set of piezoelectric members 120b to expand, as shown in FIG. 5B. Changing the voltage supply to the first and second sets of piezoelectric members 120a, 120b may change the expansion and/or contraction of the first and second sets of piezoelectric members 120a, 120b, which may cause the first and second sets of piezoelectric members 120a, 120b to be deflected at different angles relative to longitudinal axis A. While not shown, one or more lumens (e.g., a working channel, an imaging channel, etc.) may extend from handle 20, through shaft 30, and may terminate at one or more openings at the distal end face of distal end 40". These lumens may receive cables (e.g., control cables, light emitting cables, etc.) to control imaging device 100, end effectors, or the like.

A method of operating medical system 10 will be described. Medical system 10 may be inserted into a body opening (e.g., an incision, a natural orifice, etc.) and advanced to the target site as described with reference to FIG. 2. Distal end 40" may be advanced to a target site within the body. As distal end 40" is advanced through the body and/or once distal end 40" reaches the target site, an angle of one or more devices 100 may be changed by actuating devices 52. Supplying voltage to piezoelectric members 120a, 120b may cause piezoelectric members 120a, 120b to expand and/or contract, and/or bend from side to side, which may cause distal end 40" and, thus, device 100 to be angled relative to longitudinal axis A. Piezoelectric members 120a, 120b may each be independently controlled. For example, supplying voltage to piezoelectric members 120b and not supplying voltage to piezoelectric members 120a may cause distal end 40" to bend from a straight or aligned position shown in FIG. 5A to an angled position as shown in FIG. 5B. Voltage may be supplied and/or not supplied in different sequences to piezoelectric members 120a and/or 120b to cause distal end 40" to bend in different directions. Moreover, voltage may be supplied individually to each of piezoelectric members 120a or 120b, such that each of piezoelectric members 120a and 120b expand or contract differently, thereby causing different bends, e.g., different bend angles and/or bend directions. Once the medical procedure is complete, medical system 10 may be removed from the body.

While different medical systems have been described, it will be understood that the particular arrangements of elements in these medical systems are not limited. Moreover, a size and a shape of the catheter or shaft of the medical system, or the medical instruments used with the medical system, and/or the method of deploying the system, are not limited. As described in examples herein, light emitting and/or imaging devices of a medical device may be angled relative to a longitudinal axis thereof to change a light and/or viewing area for improved visualization and/or access to a target site. This may improve the results of the medical procedure, may decrease the time of the medical procedure, and may improve recovery times of the patient after the medical procedure.

It will be apparent to those skilled in the art that various modifications and variations can be made to the disclosed device without departing from the scope of the disclosure. For example, the maximum bend angle, the location of the bend in a longitudinal direction of the tube, the number of piezoelectric members and positions thereof, and/or the number of light and imaging devices may be modified based on a desired medical therapy. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    a handle including an actuation device;
    a sheath extending from the handle and having a longitudinal axis, the sheath defining an imaging lumen extending from the handle to a distal end of the sheath;
    an imaging device at the distal end of the sheath;
    a first plate positioned within the imaging lumen;
    a second plate positioned within the imaging lumen; and
    a piezoelectric member, wherein a proximal end of the piezoelectric member is connected to the first plate, wherein a distal end of the piezoelectric member is connected to the second plate, wherein movement of the piezoelectric member moves the imaging device in a first direction relative to the longitudinal axis;
    wherein the piezoelectric member expands from a first position, wherein the distal end of the piezoelectric member is disposed proximal to an opening in a distalmost end of the imaging lumen, to a second position, where the distal end of the piezoelectric member is positioned distal to the opening.

2. The device of claim 1, wherein the first plate fluidly seals a proximal end of the imaging lumen from a distal end of the imaging lumen, and wherein the piezoelectric member is connected to a distal facing surface of the first plate.

3. The device of claim 1, wherein the second plate is a flexible member fluidly sealing an opening at the distal end of the imaging lumen, wherein the distal end of the piezoelectric member is connected at a proximal facing surface of the flexible member, wherein the imaging device is connected to a distal facing surface of the flexible member, and wherein movement of the piezoelectric member causes the flexible member to bend relative to the longitudinal axis.

4. The device of claim 1, wherein the distal end of the piezoelectric member is connected to the imaging device, and wherein movement from the first position to the second position moves the imaging device from a position proximal to the distal end of the sheath to a position distal of the distalmost end of the sheath.

5. The device of claim 1, further comprising a second piezoelectric member including a proximal end and a distal end, wherein movement of the second piezoelectric member moves the imaging device in a second direction relative to the longitudinal axis, different from the first direction, and wherein the sheath further comprises a working channel extending from the handle and terminating at an opening at a distalmost end of the sheath.

6. The device of claim 5, wherein a viewing area of the imaging device includes a portion of the opening of the working channel when the imaging device is moved in one of the first direction or the second direction.

7. The device of claim 5, wherein the imaging device includes at least one of an imager and a light emitting element.

8. The device of claim 5, wherein the second plate is a flexible member fluidly sealing an opening at the distal end of the imaging lumen, wherein the distal end of each of the piezoelectric members is connected at a proximal facing surface of the flexible member, wherein the imaging device is connected to a distal facing surface of the flexible member, wherein movement of the piezoelectric members causes the flexible member to bend relative to the longitudinal axis such that the imaging device can image the opening in the working channel and a radially outer surface of a distal end face of the sheath.

9. The device of claim 8, wherein the piezoelectric members are configured to bend the flexible member in the first direction and the second direction at a same time.

10. The device of claim 9, further comprising a plurality of imaging devices, wherein a first imaging device from the plurality of imaging devices images the opening at a same time a second imaging device from the plurality of imaging devices images the radially outer surface of the distal end face.

11. The device of claim 1, wherein the piezoelectric member is in a rest state when a voltage or current is not supplied to the piezoelectric member, and wherein the piezoelectric member changes at least one of a shape, a size, or a direction when the voltage or current is supplied to the piezoelectric member.

12. A method, comprising:
    inserting a shaft of an insertion device into a body via an opening, wherein the insertion device includes a proximal plate, a distal plate at a distal end of the shaft, an imaging device connected to the distal plate, and at least one piezoelectric member extending from a first end connected to a proximal plate to a second end connected to the distal plate;
    advancing the insertion device so that a distal end of the insertion device is adjacent to a target site;
    supplying a voltage to the at least one piezoelectric member to change a viewing angle of the imaging device, wherein the viewing angle is changed toward or away from a central longitudinal axis of the insertion device; and
    advancing the insertion device so that a distal end of the insertion device is adjacent to a target site;
    supplying a voltage to the at least one piezoelectric member to change a viewing angle of the imaging device, wherein the viewing angle is changed toward or away from a central longitudinal axis of the insertion device; and
    advancing a medical instrument through a lumen of the insertion device and out of an opening in a distal end of the insertion device to perform a medical procedure;
    wherein the piezoelectric member expands from a first position, wherein the distal end of the piezoelectric member is disposed proximal to an opening in a distalmost end of the imaging lumen, to a second position, where the distal end of the piezoelectric member is positioned distal to the opening.

13. The method of claim 12, wherein the at least one piezoelectric member includes at least a first piezoelectric member and a second piezoelectric member, and wherein the method further comprises:
    supplying a first voltage to the first piezoelectric member to cause a first portion of the insertion device to be angled at a first angle relative to the central longitudinal axis; and
    supplying a second voltage, different from the first voltage, to the second piezoelectric member to cause a second portion of the insertion device, different from the first portion, to be angled at a second angle relative to the central longitudinal axis, wherein the second angle is different from the first angle.

14. The method of claim 13, wherein the distal plate is a flexible membrane connected to a perimeter of the lumen.

15. The method of claim 14, wherein the imaging device is positioned on a distal face of the flexible membrane.

* * * * *